(12) United States Patent
Cheng

(10) Patent No.: US 10,959,663 B2
(45) Date of Patent: Mar. 30, 2021

(54) DEVICE FOR DIAGNOSING AND TREATING PELVIC ORGAN PROLAPSE AND APPLICATION METHOD THEREOF

(71) Applicant: Zhejiang Baian Medical Technology Co., Ltd., Taizhou (CN)

(72) Inventor: Zhongping Cheng, Shanghai (CN)

( * ) Notice: Subject to any disclaimer, the term of this patent is extended or adjusted under 35 U.S.C. 154(b) by 245 days.

(21) Appl. No.: 16/145,005

(22) Filed: Sep. 27, 2018

(65) Prior Publication Data

US 2019/0350512 A1    Nov. 21, 2019

(30) Foreign Application Priority Data

May 18, 2018   (CN) .......................... 201810478678.9

(51) Int. Cl.
*A61B 5/00* (2006.01)
*A61B 5/107* (2006.01)

(52) U.S. Cl.
CPC .......... *A61B 5/4337* (2013.01); *A61B 5/1076* (2013.01); *A61B 5/6847* (2013.01)

(58) Field of Classification Search
CPC ....... A61B 5/43; A61B 5/4306; A61B 5/4318; A61B 5/4325; A61B 5/4331; A61B 5/4337; A61B 5/4343; A61B 5/435; A61B 5/4362; A61B 5/6847; A61B 5/107; A61B 5/1072; A61B 5/1076
See application file for complete search history.

(56) References Cited

U.S. PATENT DOCUMENTS

| | | | | |
|---|---|---|---|---|
| 9,706,948 B2 * | 7/2017 | Bhandari | ............... | A61B 5/1114 |
| 10,342,433 B2 * | 7/2019 | Froloff | .................. | A61B 5/4331 |
| 2006/0089570 A1 * | 4/2006 | Mansour | ............... | A61B 5/1076 |
| | | | | 600/591 |
| 2012/0035507 A1 * | 2/2012 | George | .................. | A61B 5/107 |
| | | | | 600/587 |
| 2017/0181687 A1 * | 6/2017 | Levin | .................... | A61B 5/4325 |
| 2019/0160332 A1 * | 5/2019 | Beer | .................... | A61B 5/4337 |

FOREIGN PATENT DOCUMENTS

CN           202526145 U    * 11/2012

OTHER PUBLICATIONS

Machine translation of CN202526145U (Year: 2020).*
English translation of Chinese Office Action in corresponding application CN201810478678.9 (Year: 2020).*

* cited by examiner

*Primary Examiner* — David J. McCrosky
(74) *Attorney, Agent, or Firm* — W&K IP

(57) ABSTRACT

Disclosed is a device for diagnosing and treating pelvic organ prolapse, including a measurement stick configured to protrude into a vagina, a distance measuring mechanism for measuring the distance from an end portion of a protruding end of the measurement stick to a hymen edge of the vagina, and an assessment mechanism. The distance measuring mechanism is connected with the assessment mechanism. The assessment mechanism includes buttons, a memory, a CPU and a display which are connected with the CPU, respectively. The device for diagnosing and treating pelvic organ prolapse provided by the present disclosure can be used in a rapid, convenient and accurate manner, which not only saves a great amount of medical resources, but also alleviates the pain index of patients during diagnosis and treatment.

7 Claims, 2 Drawing Sheets

DEVICE FOR DIAGNOSING AND TREATING PELVIC ORGAN PROLAPSE AND APPLICATION METHOD THEREOF

CROSS-REFERENCE TO RELATED APPLICATIONS

This application claims to Chinese Application No. 201810478678.9 with a filing date of May 18, 2018. The content of the aforementioned applications, including any intervening amendments thereto, are incorporated herein by reference.

TECHNICAL FIELD

The present disclosure relates to the technical field of medical devices, and more particularly, to a device for diagnosing and treating pelvic organ prolapse for a POP-Q assessment system.

BACKGROUND

Pelvic organ prolapse (POP) is a common gynecological disease that is associated with the age of females. The older the age is, the higher probability of lesions there will be. As reported by related documents, among women aged about 50, nearly 50% of them would suffer from pelvic organ prolapse. The severity assessment for pelvic organ prolapse is an important basis for the treatment of pelvic organ prolapse. As for the method for assessing the severity of pelvic organ prolapse, the American College of Obstetricians and Gynecologists formulated a pelvic organ prolapse assessment system (POP-Q) in 1995. The assessment system was acknowledged and promoted by the International Continence Society and once formulated. Today, this assessment system has already become the most widely used prolapse assessment system in foreign countries.

The POP-Q assessment system works mainly with reference to the position of the hymen edge, and under the conditions of increased abdominal pressure, the distance from the centerline of the anterior vaginal wall (corresponding to the vesicourethral fold) to the hymen edge is denoted as Aa, the distance from the centerline of the posterior vaginal wall to the hymen edge is demoted as Ap, the distance from the farthest position of the reverse fold distance Aa point of the anterior vaginal fornix to the hymen edge is denoted as Ba, the distance from the farthest position of the reverse fold distance Ap point of the posterior vaginal fornix to the hymen edge is denoted as Bp, the distance from the farthest position of the external cervical orifice to the hymen edge is denoted as C, and the distance from the position of the posterior vaginal fornix (or rectouterine pouch) to the hymen edge is denoted as D; thereafter, these parameters Aa, Ap, Ba, Bp, C and D are compared with the comparison values given by the POP-Q assessment system to obtain assessment regarding the severity of pelvic organ prolapse, thereby offering instructions for subsequent diagnosis and treatment.

After the POP-Q assessment system is applied to clinical diagnosis and treatment, the POP-Q assessment is quite troublesome due to the lack of standard dedicated tools. In view of this, the Patent Office of the People's Republic of China disclosed an invention patent No. CN107788988A entitled "Device for Measuring Severity of Female Pelvic Organ Prolapse" on Mar. 13, 2018. The device for measuring severity of female pelvic organ prolapse disclosed by this patent comprises a handheld portion and a main measurement body. The main measurement body has a first end and a second end opposite to the first end, wherein the first end is connected to the handheld portion and the second end is bent outwardly by deviating from an extension direction of the main measurement body; and the main measurement body comprises a scale zone having scales marked on the outer surface of the main measurement body; the scales comprise scale lines dividing the main measurement body into multiple zones and scale values showing the lengths. This patent only overcomes the problem of value measurement for pelvic organ prolapse and, when in use, needs to be used in cooperation with an endoscope. Moreover, after measurement, values for pelvic organ prolapse need to be recorded manually. As such, at least one to two assistants are required to help achieve the POP-Q assessment, which appears to be quite uneconomical with tremendous insufficiency of medical staff at present.

SUMMARY

In order to overcome the above defects, the technical problem to be solved by the present disclosure is about providing a device for diagnosing and treating pelvic organ prolapse and application method thereof. This device is structurally simple and user friendly, through which POP-Q assessment can be accomplished individually.

In order to solve the technical problem, the following technical solution is adopted: a device for diagnosing and treating pelvic organ prolapse and application method thereof are provided. The device for diagnosing and treating pelvic organ prolapse includes:

a measurement stick that can protrude into a vagina, a distance measuring mechanism for measuring a distance from an end portion of a protruding end of the measurement stick to a hymen edge of the vagina, and an assessment mechanism. The distance measuring mechanism is connected with the assessment mechanism.

The device for diagnosing and treating pelvic organ prolapse also includes a handle disposed on the other end of the measurement stick opposite to the protruding end and fixedly connected with the measurement stick. The handle is provided with the assessment mechanism.

The assessment mechanism includes buttons for confirming different positions of the end portion of the protruding end of the measurement stick in the vagina, a memory for recording measurement values of the distance measuring mechanism when the end portion of the protruding end of the measurement stick is at the different positions in the vagina, a CPU for calculating and determining the measurement values stored in the memory, and a display for outputting assessment results of the CPU, where the distance measuring mechanism, the buttons, the memory and the display are respectively connected with the CPU.

At least six buttons are provided, and the buttons are sequentially marked as Aa, Ap, Ba, Bp, C and D. The protruding end of the measurement stick protrudes into the vagina, and when the end portion of the protruding end of the measurement stick abuts against measurement points located at a centerline of an anterior vaginal wall, a centerline of a posterior vaginal wall, a position farthest from a reverse fold distance Aa point of an anterior vaginal fornix, a position farthest from a reverse fold distance Ap point of a posterior vaginal fornix, a position farthest from an external cervical orifice and a position of the posterior vaginal fornix in a sequential manner, the buttons marked as Aa, Ap, Ba, Bp, C and D are pressed simultaneously in a sequential manner; based on distances from the end portion of the protruding end of the measurement stick to the hymen edge measured by the distance measuring mechanism, the CPU calculates distances from each of the measurement points to the hymen edge, and stores results in the memory according to the revelation of the buttons; thereafter, the CPU compares measurement values recorded in the memory corresponding to Aa, Ap, Ba, Bp, C and D with prescribed comparison values, and outputs comparison assessment results to the display. The device for diagnosing and treating pelvic organ prolapse is provided with the measurement stick, such that the end portion of the protruding end of the measurement stick may be made to abut against a measurement point in the vagina that is required to be measured so as to form an indication point for this measurement point, thereby rendering subsequent distance measurement simple, clear and convenient. Moreover, the device for diagnosing and treating pelvic organ prolapse is provided with the distance measuring mechanism, the buttons for revealing attributes of the measurement points, the memory for automatically recording parameters of the measurement points, the CPU for conducting effective calculation and assessment for the measured data, and the display for displaying the assessment results, such that doctors engaged in diagnosis and treatment can conduct effective assessment for the condition of pelvic organ prolapse by themselves. They do not need an assistant to assist in recording any more, nor do they need to conduct comparison assessment manually. As such, human resources of hospitals can be saved.

Preferably, the distance measuring mechanism is a laser distance measuring sensor. The distance measuring mechanism may be an infrared distance measuring mechanism, an ultrasonic distance measuring mechanism or a laser distance measuring sensor, and the distance measuring mechanism of the present disclosure is preferably a laser distance measuring sensor. As one side of the measurement stick is provided with the laser distance measuring sensor on the outside of the vagina, the distance from the laser distance measuring sensor to the end portion of the protruding end of the measurement stick is a known fixed length. As such, the length of the portion of the measurement stick that protrudes into the vagina can be calculated so long as the laser distance measuring sensor measures the distance from the laser distance measuring sensor to the hymen edge. At least six buttons marked as Aa, Ap, Ba, Bp, C and D are provided, and the POP-Q assessment system includes six measurement points located respectively at the centerline of the anterior vaginal wall (corresponding to the vesicourethral fold), the centerline of the posterior vaginal wall, the position farthest from the reverse fold distance Aa point of the anterior vaginal fornix, the position farthest from the reverse fold distance Ap point of the posterior vaginal fornix, the position farthest from the external cervical orifice and the position of the posterior vaginal fornix (or rectouterine pouch). As such, when the protruding end of the measurement stick protrudes into the vagina, its end portion abuts against a measurement point in the vagina that is required to be measured. At this time, the doctor engaged in diagnosis and treatment presses a button corresponding to this measurement point with hand, and the CPU can calculate the distance from this measurement point to the hymen edge based on the distance to the hymen edge as measured by the laser distance measuring sensor, and record the measurement value in the memory revealed by the button. For example, when the end portion of the protruding end of the measurement stick abuts against the centerline of the anterior vaginal wall, the doctor engaged in diagnosis and treatment should press the button marked as "Aa", and the CPU records the calculated measurement value in the memory corresponding to "Aa". After the measurement values of all the measurement points are recorded, the CPU compares the measurement values recorded in the memory corresponding to Aa, Ap, Ba, Bp, C and D with comparison values given by the POP-Q assessment system, and presents the comparison assessment results on the display, to which a doctor may refer during subsequent treatment. During POP-Q assessment, due to the automatic recording and storage of the values of parameters Aa, Ap, Ba, Bp, C and D, and the automation of comparison assessment, doctors engaged in diagnosis and treatment do not need an assistant to assist in recording any more, nor do they need to conduct comparison assessment manually. As such, human resources of hospitals can be saved.

Preferably, an end face of the protruding end of the measurement stick is provided with a camera having its own light source. The camera is connected with the display. In the prior art, a major task of the endoscope for POP-Q assessment is to assist in finding a corresponding measurement point for the end portion of the protruding end of the measurement stick. Therefore, as compared with the cooperative endoscope, the camera, having its own light source, disposed on the end face of the protruding end of the measurement stick is capable of finding a corresponding measurement point in a more convenient, rapid and accurate manner, thereby facilitating the independent operation of doctors engaged in diagnosis and treatment.

Preferably, the handle is provided with the buttons for the assessment mechanism. In this manner, the doctor engaged in diagnosis and treatment can press the buttons while operating the measurement stick, which simplifies the operational procedure, thereby dispensing with the need for manual recording of measurement data, and saving human resources.

Preferably, the laser distance measuring sensor is disposed on a handle end face of the handle that faces toward the protruding end. Both a transmitting device and a receiving device of the laser distance measuring sensor are disposed on the handle end face of the handle that faces toward the protruding end of the measurement stick, which simplifies the arrangement structure, reduces manufacturing costs, and facilitates the operation of doctors engaged in diagnosis and treatment.

The present disclosure has the following beneficial effects: the end portion of the protruding end of the measurement stick is provided with the camera connected with the display, such that the doctor engaged in diagnosis and treatment can conveniently find the measurement point that is required to be detected, without the use of an endoscope; an outer surface or one side of the measurement stick is provided with the distance measuring mechanism, such that the doctor engaged in diagnosis and treatment doesn't need to bother to read data, thereby effectively avoiding the risk of reading data mistakenly; the handle is provided with the buttons capable of indicating the positions of the measurement points, and the memory used for storing distance data of the measurement points relative to the hymen edge, such that the doctor engaged in diagnosis and treatment doesn't need to bother to record detection data with pen. During POP-Q assessment, no endoscope is required to be used, and there is no need for manual recording of measurement data or comparison between said measurement data and comparison values given by the POP-Q assessment system. Rather, the doctor engaged in diagnosis and treatment can achieve the severity assessment for pelvic organ prolapse simply by the following manner: with the aid of a camera, the end portion of the protruding end of the detection stick is made to abut against a measurement point that is requested, by the POP-Q assessment system, to be detected; meanwhile, corresponding buttons are pressed via the handle. This can be achieved in a rapid, convenient and accurate manner, which not only saves a great amount of medical resources, but also alleviates the pain index of patients during diagnosis and treatment.

Figure 1:
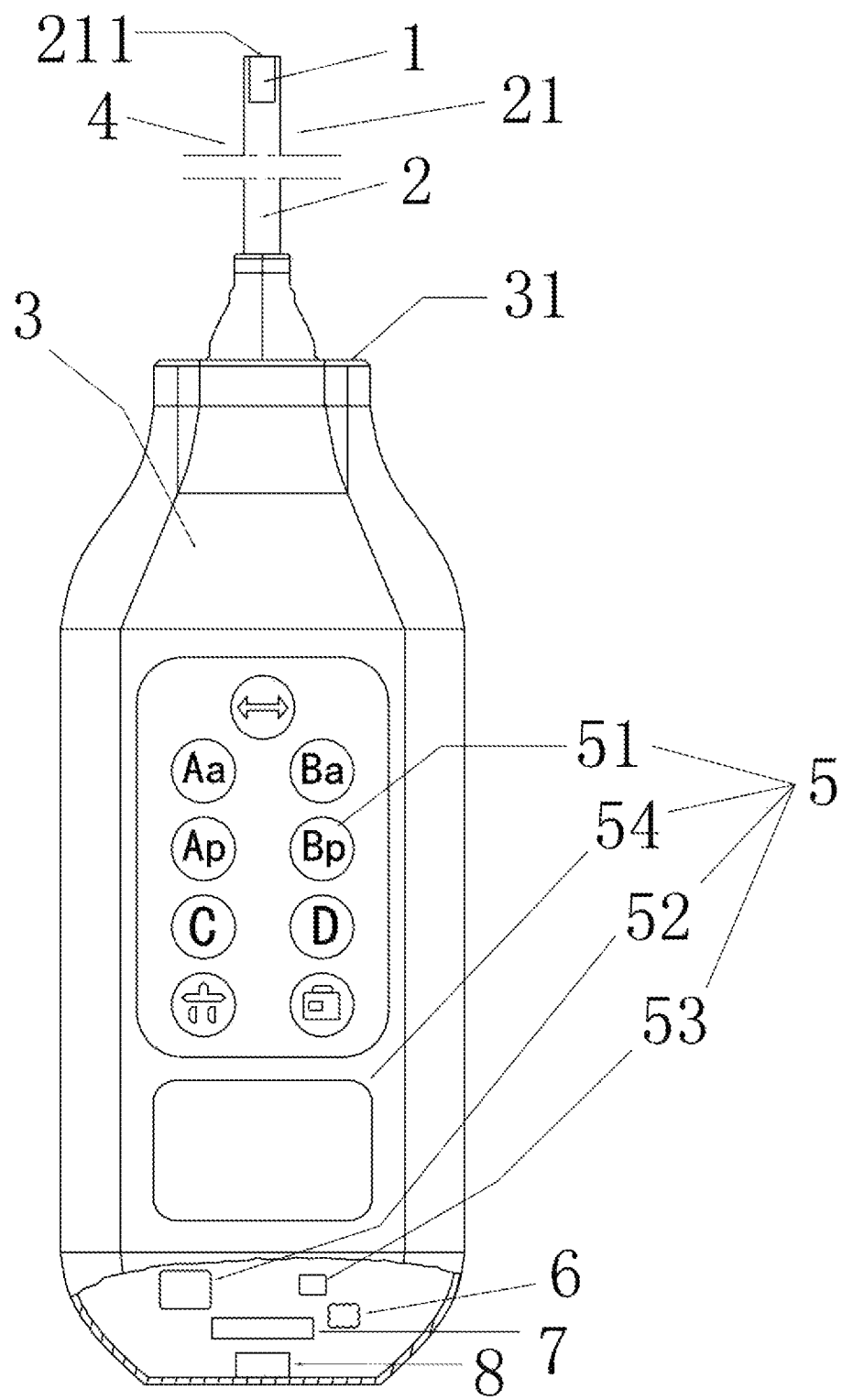
FIG. 1 is a schematic front view illustrating the structure of embodiment 1 according to the present disclosure.

In the drawings, reference numerals are illustrated as follows: 1—camera; 2—measurement stick; 21—protruding end; 211—end face of the protruding end; 3—handle; 31—handle end face; 4—distance measuring mechanism; 41—laser distance measuring sensor; 5—assessment mechanism; 51—button; 52—memory; 53—CPU; 54—display; 411—laser receiving terminal; 412—laser transmitting terminal; 6—data wireless transmission device; 7—power source; 8—data transmission and power interface.

DETAILED DESCRIPTION

In the following embodiments, a distance measuring mechanism 4 is denoted respectively as a laser distance measuring sensor 41, a photosensitive sensor 42 and a resistive ITO film 43.

Embodiment 1

Figure 2:
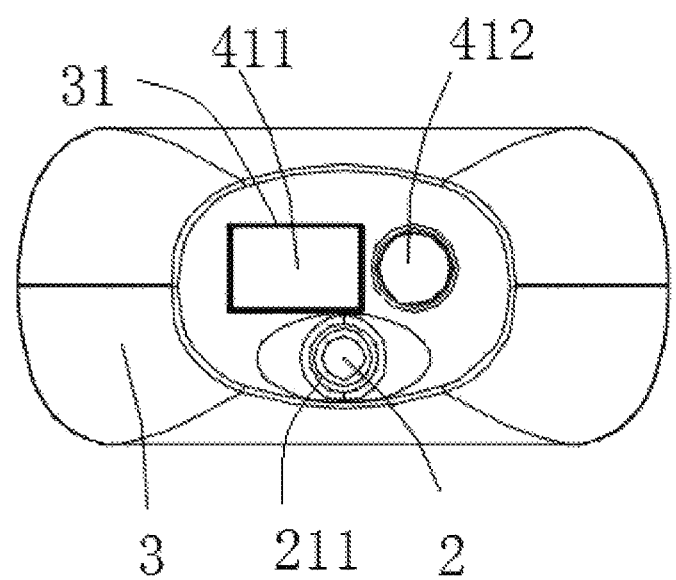
FIG. 2 is a schematic top view illustrating the structure of embodiment 1 according to the present disclosure.

As shown in FIG. 1 and FIG. 2, a device for diagnosing and treating pelvic organ prolapse was provided, including a measurement stick 2 configured to protrude into a vagina to conduct measurement, and an assessment mechanism 5. The measurement stick 2 had a length of 200 mm, and an end face 211 of the protruding end of the measurement stick 2 is provided with a camera 1 having its own light source; the camera 1 is connected with a display 54, and the brightness of the light source of the camera 1 is adjustable; the camera 1 is capable of taking pictures and recording videos; the other end of the measurement stick 2 opposite to the protruding end 21 is provided with a handle 3 fixedly connected with the measurement stick 2; the handle 3 is provided with a plurality of buttons 51, an "Aa" button 51, a "Ba" button 51, an "Ap" button 51, a "Bp" button 51, a "C" button 51 and a "D" button 51 are provided; the "Aa" button 51 indicated that the detected length is the distance from the centerline of the anterior vaginal wall (corresponding to the vesicourethral fold) to the hymen edge; the "Ba" button 51 indicated that the detected length is the distance from the farthest position of the reverse fold distance Aa point of the anterior vaginal fornix to the hymen edge; the "Ap" button 51 indicated that the detected length is the distance from the centerline of the posterior vaginal wall to the hymen edge; the "Bp" button 51 indicated that the detected length is the distance from the farthest position of the reverse fold distance Ap point of the posterior vaginal fornix to the hymen edge; the "C" button 51 indicated that the detected length is the distance from the farthest position of the external cervical orifice to the hymen edge; the "D" button 51 indicated that the detected length is the distance from the position of the posterior vaginal fornix (or rectouterine pouch) to the hymen edge; a handle end face 31 of the handle 3 facing toward the protruding end 21 of the measurement stick 2 is provided with a laser transmitting terminal 411 and a laser receiving terminal 412 of a laser distance measuring sensor 41; the laser distance measuring sensor 41 conducted distance measurement in a direction facing toward the hymen edge of the vagina; the assessment mechanism 5 included the buttons 51 for confirming positions of the end portion of the protruding end 21 of the measurement stick in the vagina, a memory 52 for recording the measurement values of the measurement stick 2 when the end portion of the protruding end 21 of the measurement stick 2 was located at the positions in the vagina, a CPU 53 for determining and calculating the measurement values stored in the memory 52 according to norms and requirements, and a display 54 for outputting the assessment results of the CPU 53; the display is a computer screen, and the laser distance measuring sensor 41, the buttons 51 and the memory 52 all are connected with the CPU 53; the memory 52 and the CPU 53 are also disposed in the handle 3, and the CPU 53 is connected with the computer screen via a data wireless transmission device 6; the handle is further provided with a power source 7 for powering the camera 1, the memory 52, the CPU 53 and the data wireless transmission device 6, and the power source 7 is a battery or a charging circuit and is charged through the data transmission and power interface 8.

In another alternative mode, the CPU 53 is connected with an external computer display screen or a printer through the data wireless transmission device 6 or the data transmission and power interface 8 to display or print data.

Application method: the protruding end 21 of the measurement stick 2 is configured to protrude into the vagina, and when the end portion of the protruding end 21 of the measurement stick 2 abutted against the centerline of the anterior vaginal wall, the centerline of the posterior vaginal wall, the position farthest from the reverse fold distance Aa point of the anterior vaginal fornix, the position farthest from the reverse fold distance Ap point of the posterior vaginal fornix, the position farthest from the external cervical orifice and the position of the posterior vaginal fornix in a sequential manner, the buttons 51 marked as Aa, Ap, Ba, Bp, C and D were pressed simultaneously in a sequential manner; the CPU 53 can calculate the distances from each of the measurement points to the hymen edge based on the distances to the hymen edge measured by the laser distance measuring sensor 41, and record measurement values in the memory 52 revealed by the buttons 51; thereafter, the CPU 53 compared the measurement values recorded in the memory 52 corresponding to Aa, Ap, Ba, Bp, C and D with prescribed comparison values, and outputted comparison assessment results to the display 54. When required, assessment results may be printed out in the form of a detection report.

What is claimed is:

1. A device for diagnosing and treating pelvic organ prolapse, comprising:
a measurement stick protruding into a vagina;
a distance measuring mechanism for measuring a distance from an end portion of a protruding end of the measurement stick to a hymen edge of the vagina; and
an assessment mechanism;
wherein the distance measuring mechanism is connected with the assessment mechanism;
the device for diagnosing and treating pelvic organ prolapse also comprises a handle disposed on the other end of the measurement stick opposite to the protruding end and fixedly connected with the measurement stick; the handle is provided with the assessment mechanism; the assessment mechanism comprises buttons for confirming different positions of the end portion of the protruding end of the measurement stick in the vagina, a memory for recording measurement values of the distance measuring mechanism when the end portion of the protruding end of the measurement stick is at the different positions in the vagina, a CPU for calculating and determining the measurement values stored in the memory, and a display for outputting assessment results of the CPU; and the distance measuring mechanism, the buttons, the memory and the display are connected to the CPU;

wherein at least six buttons are provided; and the buttons are sequentially marked as Aa, Ap, Ba, Bp, C and D.

2. The device for diagnosing and treating pelvic organ prolapse of claim 1, wherein an end face of the protruding end of the measurement stick is provided with a camera having its own light source; and the camera is connected with the display.

3. The device for diagnosing and treating pelvic organ prolapse of claim 2, wherein the distance measuring mechanism is a laser distance measuring sensor.

4. The device for diagnosing and treating pelvic organ prolapse of claim 3, wherein the laser distance measuring sensor is disposed on a handle end face of the handle facing toward the protruding end.

5. The device for diagnosing and treating pelvic organ prolapse of claim 1, wherein the distance measuring mechanism is a laser distance measuring sensor.

6. The device for diagnosing and treating pelvic organ prolapse of claim 5, wherein the laser distance measuring sensor is disposed on a handle end face of the handle facing toward the protruding end.

7. An application method of the device for diagnosing and treating pelvic organ prolapse of claim 1, wherein the protruding end of the measurement stick protrudes into the vagina, and when the end portion of the protruding end of the measurement stick abuts against measurement points located at a centerline of an anterior vaginal wall, a centerline of a posterior vaginal wall, a position farthest from a reverse fold distance Aa point of an anterior vaginal fornix, a position farthest from a reverse fold distance Ap point of a posterior vaginal fornix, a position farthest from an external cervical orifice and a position of the posterior vaginal fornix in a sequential manner; and the buttons marked as Aa, Ap, Ba, Bp, C and D are pressed simultaneously in a sequential manner; based on distances from the distance measuring mechanism to the hymen edge measured by the distance measuring mechanism, the CPU calculates distances from each of the measurement points to the hymen edge, and stores results in the memory according to the revelation of the buttons; and the CPU compares the measurement values recorded in the memory corresponding to Aa, Ap, Ba, Bp, C and D with prescribed comparison values, and outputs comparison assessment results to the display.

* * * * *